(12) United States Patent
Margot et al.

(10) Patent No.: US 6,737,396 B2
(45) Date of Patent: May 18, 2004

(54) USE OF (1-ETHOXYETHOXY) CYCLODODECANE IN A PERFUME COMPOSITION AS PERFUME FIXATIVE AND/OR ENHANCER

(75) Inventors: Christian Margot, Gilly (CH); Pierre-Alain Blanc, Crassier (CH)

(73) Assignee: Firmenich SA, Geneva (CH)

( * ) Notice: Subject to any disclaimer, the term of this patent is extended or adjusted under 35 U.S.C. 154(b) by 5 days.

(21) Appl. No.: 10/318,204

(22) Filed: Dec. 13, 2002

(65) Prior Publication Data

US 2003/0130163 A1 Jul. 10, 2003

Related U.S. Application Data

(63) Continuation-in-part of application No. PCT/IB01/01048, filed on Jun. 13, 2001.

(30) Foreign Application Priority Data

Jul. 10, 2000 (CH) ..................................... 2000 1354/00

(51) Int. Cl.$^7$ .................................................. A61K 7/46
(52) U.S. Cl. ............................................. 512/8; 512/25
(58) Field of Search ....................................... 512/8, 25

(56) References Cited

U.S. PATENT DOCUMENTS

| 3,993,697 A | 11/1976 | Bruns et al. ............. 260/611 R |
| 4,990,495 A | 2/1991 | Giersch et al. ................. 512/8 |
| 6,420,334 B1 * | 7/2002 | Surburg et al. ............... 512/25 |

FOREIGN PATENT DOCUMENTS

FR  1 393 647  7/1965

* cited by examiner

Primary Examiner—Jill Warden
Assistant Examiner—Monique T. Cole
(74) Attorney, Agent, or Firm—Winston & Strawn LLP

(57) ABSTRACT

The invention concerns (1-ethoxyethoxy-cyclododecane) which, although its smell is not noticed by a large number of people, can advantageously be used in a perfume composition as perfume exalting fixative.

6 Claims, No Drawings

USE OF (1-ETHOXYETHOXY) CYCLODODECANE IN A PERFUME COMPOSITION AS PERFUME FIXATIVE AND/OR ENHANCER

CROSS-REFERENCE TO RELATED APPLICATIONS

This application is a continuation-in-part of the U.S. national phase designation of International Application PCT/IB01/01048 filed Jun. 13, 2001.

BACKGROUND ART

The present invention relates to the perfumery industry. It concerns more particularly the use of (1-ethoxyethoxy) cyclododecane in a perfuming composition, as perfume fixative and/or enhancer.

U.S. Pat. No. 3,993,697 describes via a general formula a number of acetals substituted by a cycloalkyl group and possessing an odor of the amber woody type. Although (1-ethoxyethoxy)cyclododecane is comprised in the general formula disclosed in said patent and is mentioned in the list of odorant compounds, (1-ethoxyethoxy)cyclododecane is also described as not being amongst the most odorant and appropriate compounds for use as a perfuming ingredient. The odor of (1-ethoxyethoxy) cyclododecane is not specifically disclosed in said document, and although there is disclosed a method of synthesis which can be applied for all the compounds falling into the general formula, the preparation of the invention's compound is not specified in any example, and said compound is not used in any of the perfumery examples described.

Therefore, in view of said document, it appears that (1-ethoxyethoxy)cyclododecane has not been detected as being interesting from an olfactive perspective and one can even wonder whether the inventors had the compound in their hands or not. Some tests described in the examples given further below and done by expert perfumers or panelists, will confirm the fact that the invention's compound turns out to be weakly odorant and even totally devoid of odor for part of the population.

SUMMARY OF THE INVENTION

The present invention is directed towards a method to fix or exalt the odor properties of a perfuming composition or a perfumed article, which method comprises adding to the composition or article an effective amount of (1-ethoxyethoxy)cyclododecane.

Another aspect of the invention provides perfuming compositions or perfumed articles containing (1etoxyethoxy) cyclododecane as a perfume exalting fixative.

DETAILED DESCRIPTION OF THE PREFERRED EMBODIMENTS

Now, despite the fact that the odor of (1-ethoxyethoxy) cyclododecane is perceivable only by a minority of people, we have discovered that, surprisingly, said compound provides a technical effect which is both new and unexpected, recognized in a general manner even by those who are anosmic to the pure compound, when said compound is used in composition. We have thus been able to establish that (1-ethoxyethoxy)cyclododecane can, in a very advantageous way, be used in a perfuming composition as a perfume exalting fixative, while providing to the composition's fragrance a nice woody connotation. By "fixative" we mean here an ingredient capable of improving a perfume by a complex technical effect which results in an effect which is simultaneously characterized by roundness, substantivity, dimension or volume, or still olfactive richness provided by this compound to the composition's odor.

In addition to its fixing action, (1-ethoxyethoxy) cyclododecane possesses also an fixing or exalting effect of some odorant notes of the composition into which it is added, such as in particular the notes of the musky and aromatic type.

It has also been observed that, while most people do not smell the invention's compound as such, said compound brings advantageously to the compositions into which it is added a very nice odorant note of the woody type which is generally perceived by all. Incidentally, we can emphasize the fact that the effect produced by the invention's compound is quite different from the one produced by the preferred compounds disclosed in U.S. Pat. No. 3,993,697. For example (methoxymethoxy)cyclododecane, a compound particularly appreciated for its olfactive qualities according to the cited document, possesses a very powerful odor of the woody and ambery type. This compound must be used in very small quantities due to its strength and does not provide any volume or dimension to the composition to which it is added. The effect of (1-ethoxyethoxy) cyclododecane which, as such, turns out to be practically useless, is much more subtle in composition and, besides a woody type odor, particularly interesting for perfumery, it provides a fixative effect such as defined above and a perfume exaltation, thus imparting a new dimension to the odor of the composition containing it. In other terms, the compositions into which (1-ethoxyethoxy)cyclododecane is added acquire a perfume quality which is expressed at the same time by a roundness of the odorant note and a dimension and intensity which is difficult to obtain with perfuming ingredients customarily known for their woody odor.

Thus, thanks to its exalting fixative property, (1-ethoxyethoxy)cyclododecane, unlike a "classic" perfuming ingredient, does not produce just the effect of adding a particular odorant note to a mixture in order to modulate the odor of the latter. The technical effect produced by the invention's compound is of a more complex nature, as it has been described above. The comparative tests presented further below show the effect of the invention's compound in composition, compared with "classic" perfuming ingredients known for their woody odor. In the present case, it is a question of really a new technical effect, which is also very useful for the perfumers.

The perfuming compositions into which the inventive compound is added in order to impart, at the same time, an intensity, roundness, richness and substantivity, are mixtures of perfuming ingredients commonly used in perfumery and possibly one or more solvents commonly used in perfuming compositions. Therefore, a perfuming composition according to the invention comprises the invention's compound together with at least two perfuming co-ingredients and possibly one or more solvents.

The nature and type of these perfuming co-ingredients do not warrant a more detailed description here, which in any case would not be exhaustive, the skilled person being able to select them on the basis of its general knowledge and according to the nature of the product to be perfumed and the desired olfactory effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the art of perfumery.

Similarly, a detailed description of the nature and type of solvents commonly used in perfuming compositions cannot be exhaustive. A skilled person is able to select them on the basis of the nature of the product to be perfumed. However, as non-limiting examples of such solvents, one can cite dipropyleneglycol, diethyl phthalate, isopropyl myristate, benzyl benzoate, 2-(2-ethoxyethoxy)-1-ethanol or ethyl citrate as well as ethanol, water/ethanol mixtures, limonene or other terpenes, isoparaffins such as those known under the trademark Isopar RTM. (origin: Exxon Chemical) or glycol ethers and glycol ether esters such as those known under the trademark Dowanol RTM. (origin: Dow Chemical Company).

The compositions containing (1-ethoxyethoxy) cyclododecane according to the invention are suitable for use in fine perfumery articles, such as in perfumes, colognes or after-shave lotions, as well as in other current uses in functional perfumery articles such as perfumed soaps, shower or bath gels, hygiene products, or hair care products such as shampoos or conditioners, body deodorants and air fresheners or cosmetic preparations.

The perfuming compositions according to the invention can also be used in articles such as liquid or solid detergents for textile treatment, fabric softeners, or also in detergent compositions or cleaning products for cleaning dishes or varied surfaces, for industrial or household use.

Said fine or functional perfumery articles are also referenced as perfumed articles.

The proportions in which (1-ethoxyethoxy) cyclododecane can be incorporated in the different products mentioned above vary in a broad range of values. These values depend on the nature of the article or product that has to be perfumed and on the olfactory effect sought, namely the intensity of some odorant notes, roundness, volume, substantivity, richness of the final odor, as well as on the nature of the coingredients in a given composition. It has been mentioned above that (1-ethoxyethoxy)cyclododecane in composition was particularly advantageous to reinforce the musky and aromatic notes.

As examples, one can cite typical concentrations from 2 to 30% by weight of the compound with respect to the weight of the perfuming composition in which it is incorporated.

(1-ethoxyethoxy)cyclododecane may be prepared in one step from cyclododecanol in the presence of ethyl-vinyl-ether and of an acidic catalyst. The specific conditions of the reaction will be described in more detail in one of the following examples.

EXAMPLES

The invention will now be described in further detail by way of the following examples, wherein the temperatures are indicated in degrees Celsius (° C.) and the abbreviations have the usual meaning in the art.

Example 1

Preparation of (1-ethoxyethoxy)cyclododecane

In a 3 l reactor containing 1.25 l of methyl-tert-butyl ether were introduced 300 g (1.62 mol) of cyclododecanol (origin: Fluka) and dissolved by heating the mixture at 35°. After cooling at 10°, a partial recrystallization was observed (thin crystals). After the addition of approximately 20 mg of p-toluenesulfonic acid, 240 ml of ethyl-vinyl-ether were introduced over 2 hours using an addition-funnel, while maintaining the temperature between 10 and 15°. The temperature was maintained at 15° soon after the end of the addition. At the end of the reaction, the mixture was washed with 100 ml of a 5% aqueous NaOH and the mixture was decanted. The solvent was evaporated under vacuum while maintaining the temperature below or at 15°. A distillation under high vacuum (Bp 135°, 1.3 Pa) allowed to obtain, with a yield of 70%, 281 g of a colorless product having a purity of 98.5%.

Analytical data:

IR: 2933(s); 1471(m); 1445(w); 1376(w); 1130, 1100(s)
SM 256(M+, <1%): 241(1%); 227(5%); 73(100%)
$^1$H-RMN(360 MHz, CDCl$_3$): 4.73(q, J=5.5, 1H); 3.72 (hept, J=4.0, 1H); 3.6(m, 2H); 1.6(m, 2H); 1.3–1.5(m, 20H); 1.30(d, J=5.5, 3H); 1.20(t, J=7.1, 3H).
$^{13}$C-NMR(90 MHz, CDCl$_3$): 98.3(d); 73.5(d); 59.9(t); 30.2(t); 29.5(t); 24.6(2t); 24.1(t); 23.5(t); 23.4(t); 23.2(t); 23.1(t); 21.2(t); 20.9(q); 20.7(t); 15.4(q).

Example 2

Comparison of the effect of (1-ethoxyethoxy) cyclododecane alone with the effect of Iso E super alone [1-(octahydro-2,3,8,8-tetramethyl-2-naphthalenyl-1-ethanone; origin: International Flavors and Fragrances, USA]

Two sets of linen (70% cotton and 30% synthetic) containing each 18 terry towels of 30×30 cm and various textiles were washed separately at 40° in a washing machine (Miele, semi-professional model S5425), without pre-wash, and using 85 g of a VIA Taed Sensitive (origin: Lever, Stockholm) detergent base type comprising respectively 0.2% of (1-ethoxyethoxy)cyclododecane in one case, and 0.2% of Iso E super in the other case. A group of 40 panelists judged the intensity of the woody note of (1-ethoxyethoxy) cyclododecane in comparison with Iso E super using an intensity scale ranging from 1 (weakest) to 7 (most powerful), firstly of the washing powder, then of the dry linen (24 h of drying at approximately 60% relative humidity and a temperature of 21°) and finally of the wet linen.

The following table indicates the number of panelists having chosen specific intensity ranges of the woody note for each of the 2 ingredients tested:

TABLE 1

| | Powder | | Wet linen | | Dry linen | |
|---|---|---|---|---|---|---|
| | Number of panelists | | | | | |
| Intensity | (1-ethoxy-ethoxy) cyclo-dodecane | Iso E super | (1-ethoxy-ethoxy) cyclo-dodecane | Iso E super | (1-ethoxy-ethoxy) cyclo-dodecane | Iso E super |
| <2 | 11 | 2 | 7 | 4 | 19 | 7 |
| 2–3 | 9 | 2 | 9 | 3 | 8 | 3 |
| 3–4 | 1 | 5 | 9 | 0 | 0 | 2 |
| 4–5 | 10 | 10 | 4 | 7 | 6 | 7 |
| 5–6 | 3 | 14 | 8 | 16 | 6 | 12 |
| ≧6 | 6 | 7 | 3 | 10 | 1 | 9 |

In view of the above table it clearly appears that two populations are clearly distinguishable in what concerns the perception of (1-ethoxyethoxy)cyclododecane. Indeed, to the contrary of Iso E super which is generally well perceived by most of the panelists, we can notice that a number of said panelists do not perceive at all or little the invention compound (intensity between 1 and 3), and that conversely exist some persons who perceive it better (intensity between 5 and 6).

Example 3

Comparative example, in composition, between (1-ethoxyethoxy)cyclododecane and two compounds having a woody connotation The following example compares the effect in composition of (1-ethoxyethoxy)cyclododecane with that of compounds known to confer a woody note to the compositions into which they are added, namely Iso E super [1-(octahydro-2,3,8,8-tetramethyl-2-naphtalenyl)-1-ethanone; origin: International Flavors and Fragrances, USA], and Vertofix (origin: International Flavors and Fragrances, USA). The two compounds cited for the comparison with the invention's compound are commonly used in the field of perfumery.

A panel of expert perfumers evaluated, on a blind test, on the one hand, the preference and, on the other hand, the woody note of the 3 compounds respectively in two compositions. The composition A consisted of the following ingredients:

| Ingredients | Parts by weight |
|---|---|
| 10% * Bornyl acetate | 15 |
| 10% * Geranyl acetate | 35 |
| Linalyl acetate | 70 |
| 10% * Methyl nonyl acetaldehyde | 20 |
| 10% * Amyl allyl glycolate | 15 |
| Methyl anthranilate | 5 |
| Artemisia essential oil | 10 |
| Bacdanol ® [1] | 25 |
| Bergamote essential oil | 15 |
| 10% * Ceylon Cinnamon essential oil | 70 |
| 10% * Castoreum essential oil | 30 |
| 10% * Citral [2] | 20 |
| Coumarine | 240 |
| Cumin essential oil | 30 |
| Dihydromyrcenol [3] | 270 |
| 10% * Eugenol | 15 |
| Orange flower essential oil | 30 |
| Galaxolide ® [4] | 1100 |
| Geraniol | 10 |
| Lavender essential oil | 30 |
| Lavandin grosso essential oil | 60 |
| Lilial ® [5] | 230 |
| Linalool | 70 |
| Lyral ® [6] | 170 |
| 10% * Spearmint essential oil | 30 |
| Iso-methyl-alpha-ionone | 100 |
| 10% * White thyme essential oil | 25 |
| Tonalide ® [7] | 750 |
| 1% * Triplal ® [8] | 20 |
| Vanilline | 90 |
| Total | 3600 |

* in dipropylene glycol
[1] 2-ethyl-4-(2,2,3-trimethyl-3-cyclopenten-1-yl)-2-butenol; origin: International Flavors and Fragrances
[2] origin: Firmenich SA, Geneva, Switzerland
[3] origin: International Flavors and Fragrances, USA
[4] 1,3,4,6,7,8-hexahydro-4,6,6,7,8,8-hexamethyl-cyclopenta-γ-2-benzopyrane; origin: International Flavors and Fragrances, USA
[5] 3-(4-tert-butylphenyl)-2-methylpropanal; origin: Givaudan-Roure SA, Geneva, Switzerland
[6] mixture of 4-(4-hydroxy-4-methylpentyl)-3-cyclohexen-1-carbaldehyde et 3-(4-hydroxy-4-methylpentyl)-3-cyclohexen-1-carbaldehyde; origin: International Flavors and Fragrances, USA
[7] (5,6,7,8-tetrahydro-3,5,5,6,8,8-hexamethyl-2-naphtyl)-1-ethanone; origin: Polak's Frutal Works, Holland
[8] 2,4-dimethyl-3-cyclohexen-1-carboxaldehyde; origin: International Flavors and Fragrances To this base composition there were added respectively 700 parts by weight of each of the three ingredients to be tested and the three new compositions were evaluated on a blind test by a panel of 9 expert perfumers, of which only 2 had perceived the woody note of (1-ethoxyethoxy) cyclododecane when used alone.

The composition B consisted of the following ingredients:

| Ingredients | Parts by weight |
|---|---|
| Carbinol acetate | 30 |
| Dodecyl acetate | 50 |
| Geranyl acetate | 10 |
| Styrallyl acetate | 10 |
| Hexylcinnamic aldehyde | 150 |
| γ-Undecalactone | 10 |
| Benzylacetone | 30 |
| Verdyl acetate | 70 |
| Coumarine | 5 |
| 10% * α-Damascone | 30 |
| Dihydromyrcenol [1] | 70 |
| Habanolide ® [2] | 140 |
| Iralia ® [3] | 40 |
| Lavandin grosso essential oil | 25 |
| 10% *1-(5,5-Dimethyl-1-cyclohexen-1-yl)-4-penten-1-one [4] | 10 |
| Phenethylol | 100 |
| Hexyl salicylate | 250 |
| Undecavertol ® [5] | 10 |
| Violet essential oil | 20 |
| Wardia ® [6] | 40 |
| Total | 1100 |

* in dipropyleneglycol
[1] origin: International Flavors and Fragrances
[2] pentadecenolide; origin: Firmenich SA, Geneva, Switzerland
[3] mixture of methylionones isomers; origin: Firmenich SA, Geneva, Switzerland
[4] origin: Firmenich SA, Geneva, Switzerland
[5] 4-methyl-3-decen-5-ol; origin: Givaudan-Roure, Vernier, Switzerland
[6] origin: Firmenich SA, Geneva, Switzerland To this base composition there were added respectively 300 parts by weight of each of the three ingredients to be tested and the three new compositions were evaluated on a blind test by a panel of 7 expert perfumers, of which only 2 had described (1-ethoxyethoxy)cyclododecane as having a woody odor.

The two following tables show, for each of the three compounds, the number of expert perfumers having classified, on criteria of preference and woody note, in first, second and respectively third position each of the three samples submitted.

TABLE 2

| | COMPOSITION A | | | | | |
|---|---|---|---|---|---|---|
| | Preference | | | Woody note | | |
| Added ingredient | 1st position | 2nd position | 3rd position | 1st position | 2nd position | 3rd position |
| (1-Ethoxy-ethoxy)-cyclododecane | 6 | 2 | 1 | 4 | 3 | 2 |
| Iso E super | 3 | 1 | 5 | 4 | 3 | 2 |
| Vertofix | 0 | 6 | 3 | 1 | 3 | 5 |

TABLE 3

| | COMPOSITION B | | | | | |
|---|---|---|---|---|---|---|
| | Preference | | | Woody note | | |
| Added ingredient | 1st position | 2nd position | 3rd position | 1st position | 2nd position | 3rd position |
| (1-Ethoxy-ethoxy)-cyclododecane | 4 | 0 | 3 | 3 | 2 | 2 |

TABLE 3-continued

COMPOSITION B

| Added ingredient | Preference | | | Woody note | | |
|---|---|---|---|---|---|---|
| | 1st position | 2nd position | 3rd position | 1st position | 2nd position | 3rd position |
| Iso E super | 1 | 3 | 3 | 3 | 2 | 2 |
| Vertofix | 2 | 4 | 1 | 1 | 3 | 3 |

It emerges from these two tables on the one hand, that (1-ethoxyethoxy)cyclododecane is preferred by a majority of perfumers (6/9 and 4/7) to the two other compounds, which are known from the prior art and used to confer an olfactive effect of the same type. Moreover, concerning in particular the woody note, it appears that the compound of the invention, which is not perceived, or is weakly perceived, by more than 50% of the persons, is fully comparable, in respect of the woody note which is revealed in composition, to the compounds generally used and which are perceived, even pure, by all the persons.

Example 4

Preparation of a perfuming composition for a "woody-herbaceous" type, masculine, eau de toilette A base composition for a masculine eau de toilette was prepared by admixing the following ingredients:

| Ingredients | Parts by weight |
|---|---|
| Linalyl acetate | 360 |
| 10% * Ambrinol | 20 |
| Sfuma lemon essential oil | 600 |
| Coumarin | 60 |
| 10% * α-Damascone | 60 |
| Dihydromyrcenol [1] | 660 |
| Tarragon essential oil | 20 |
| 10% * Farenal [2] | 30 |
| Polysantol ® [3] | 40 |
| Geraniol | 40 |
| Chinese geranium essential oil | 120 |
| Hedione ® HC [4] | 300 |
| Laurel essential oil | 10 |
| Linalool | 200 |
| Lyral ® [5] | 100 |
| Muscenone [6] | 100 |
| Trans-1-(2,2,6-trimethyl-1-cyclohexyl)-3-hexanol [7] | 50 |
| Tonalide ® [8] | 410 |
| Vanilline | 20 |
| Total | 3200 |

* in dipropyleneglycol
[1] origin: International Flavors and Fragrances, USA
[2] 2,6,10-trimethyl-9-undecenal; origin: Haarmann & Reimer
[3] 3,3-dimethyl-5-(2,2,3-trimethyl-3-cyclopenten-1-yl)-4-penten-2-ol; origin: Firmenich SA, Geneva, Switzerland
[4] methyl dihydrojasmonate having a high contains in the cis isomer; origin: Firmenich SA, Geneva, Switzerland
[5] mixture of 4-(4-hydroxy-4-methylpentyl)-3-cyclohexene-1-carbaldehyde and 3-(4-hydroxy-4-methylpentyl)-3-cyclohexene-1-carbaldehyde; origin: International Flavors and Fragrances, USA
[6] 3-methyl-cyclopentadecenone; origin: Firmenich SA, Geneva, Switzerland
[7] origin: Firmenich SA, Geneva, Switzerland
[8] (5,6,7,8-tetrahydro-3,5,5,6,8,8-hexamethyl)-1-ethanone; origin: Polak's Frutal Works, Holland The addition of 100 parts by weight of (1-ethoxyethoxy)cyclododecane to the above-mentioned eau de toilette for men imparted to the composition a soft ambery-woody note, while providing a volume and an exceptional substantivity to said fragrance composition. Moreover, the addition of the invention's compound results in highlighting, in a clearly more intense way, the masculine note of the composition and also in rendering the latter richer than when (1-ethoxyethoxy)cyclododecane is absent.

Example 5

Preparation of a perfuming composition for an "aromatic" type, masculine, eau de toilette The addition of 700 parts by weight of (1-ethoxyethoxy)cyclododecane to composition A described in example 3 imparted to said base composition a new dimension. Indeed the fragrance of the new composition, resulting from the addition of the invention's compound, became more complex, warmer, more woody and the aromatic notes were clearly exalted.

Example 6

Preparation of a perfuming composition for a "floral-green" type detergent base

A perfuming composition for a detergent base was prepared by admixing the following ingredients:

| Ingredients | Parts by weight |
|---|---|
| Cyclanol acetate | 10 |
| Verdyl acetate | 300 |
| 10% * Amyl allyl glycolate | 60 |
| 4-Cyclohexyl-2-methyl-2-butanol [1] | 100 |
| Dihydromyrcenol [2] | 1600 |
| Polysantol ® [3] | 20 |
| Galaxolide ® [4] | 900 |
| Geranyl nitrile | 10 |
| Linalool | 150 |
| 10% * Isopropyl methylbutyrate | 150 |
| 10% * Myrcene | 50 |
| 1% * 1-(5,5-dimethyl-1-cyclohexen-1-yl)-4-penten-1-one [5] | 30 |
| α-Terpineol | 40 |
| γ-Undecalactone | 10 |
| Verdox ® [6] | 570 |
| Total | 4000 |

* in dipropyleneglycol
[1] origin: Firmenich SA, Geneva, Switzerland
[2] origin: International Flavors and Fragrances, USA
[3] 3,3-dimethyl-5-(2,2,3-trimethyl-3-cyclopenten-1-yl)-4-penten-2-ol; origin: Firmenich SA, Geneva, Switzerland
[4] 1,3,4,6,7,8-hexahydro-4,4,6,7,8,8-hexamethyl-cyclopenta-γ-2-benzopyrane; origin: International Flavors and Fragrances, USA
[5] origin: Firmenich SA, Geneva, Switzerland
[6] 2-tert-butyl-1-cyclohexyl acetate; origin: International Flavors and Fragrances, USA The addition of 900 parts by weight of (1-ethoxyethoxy)cyclododecane to this base composition for detergents produced two effects: on the one hand, the odor of the composition after the addition of said compound became richer, warmer, and was well appreciated for its very nice woody connotation. On the other hand, after the washing, an evaluation carried out by a panel of 22 perfumers showed that the intensity and the softness of the composition containing the (1-ethoxyethoxy)cyclododecane was far superior to that of the initial composition. Indeed, over the 22 perfumers, all chose the composition according to the present invention, while 11 perfumers of the same panel did not perceive the compound as such and one perfumer perceived it quite weakly.

What is claimed is:
1. A method to fix or exalt the odor properties of a perfuming composition or a perfumed article that contains a perfuming ingredient, which method comprises adding to said composition or article a fragrance fixing or exalting amount of (1-ethoxyethoxy)cyclododecane sufficient to exalt the odor of the perfuming ingredient.

2. The method according to claim 1, wherein the perfuming ingredient imparts aromatic and musky type odor notes to the composition or article and the (1-ethoxyethoxy)cyclododecane exalts perception of said aromatic and musky type odorant notes.

3. The method according to claim 1, wherein the amount of (1-ethoxyethoxy)cyclododecane added to the perfuming composition is from 2 to 30% by weight, with respect to the weight of the perfuming composition.

4. Perfuming composition or perfumed article that contains a perfuming ingredient and further containing (1-ethoxyethoxy)cyclododecane as a perfume exalting fixative in an amount sufficient to exalt the odor of the perfuming ingredient.

5. Perfumed composition according to claim 4, wherein the (1-ethoxyethoxy)cyclododecane is present in an amount of from 2 to 30% by weight with respect to the weight of the perfuming composition.

6. Perfumed article according to claim 4, in the form of a perfume or cologne, an after-shave lotion, a cosmetic preparation, a soap, a shampoo or conditioner or other hair care product, a shower or bath gel, a body deodorant, an air freshener, a detergent, a fabric softener or a household product.

* * * * *

UNITED STATES PATENT AND TRADEMARK OFFICE
CERTIFICATE OF CORRECTION

PATENT NO. : 6,737,396 B2
DATED : May 18, 2004
INVENTOR(S) : Margot et al.

It is certified that error appears in the above-identified patent and that said Letters Patent is hereby corrected as shown below:

Title page,
Item [57], ABSTRACT,
Line 1, change "(1-ethoxyethoxy-cyclododecane)" to
-- (1-ethoxyethoxy)cyclododecane --.
Line 4, before "perfume exalting fixative." insert -- a --.

Column 1,
Line 49, change "(1etoxyethoxy)" to -- (1-ethoxyethoxy) --.

Column 3,
Line 10, change "Isopar RTM." to -- Isopar® --; and
Line 12, change "Dowanol RTM." to -- Dowanol® --.

Column 10,
Line 4, change "Perfumed" to -- Perfuming --

Signed and Sealed this

Twenty-third Day of November, 2004

JON W. DUDAS
*Director of the United States Patent and Trademark Office*